United States Patent
Jung et al.

(10) Patent No.: US 10,234,435 B2
(45) Date of Patent: Mar. 19, 2019

(54) CONDUCTIVITY DETECTOR AND ION CHROMATOGRAPHY SYSTEM INCLUDING THE SAME

(71) Applicants: Sunghan Jung, Hwaseong-si (KR); Ami Choi, Hwaseong-si (KR); JungDae Park, Yongin-si (KR); Dong-Soo Lee, Seoul (KR); Ji-Won Eom, Seoul (KR); Kyung-Soo Chae, Seoul (KR); Kwang-Shin Lim, Yongin-si (KR)

(72) Inventors: Sunghan Jung, Hwaseong-si (KR); Ami Choi, Hwaseong-si (KR); JungDae Park, Yongin-si (KR); Dong-Soo Lee, Seoul (KR); Ji-Won Eom, Seoul (KR); Kyung-Soo Chae, Seoul (KR); Kwang-Shin Lim, Yongin-si (KR)

(73) Assignees: Samsung Electronics Co., Ltd., Suwon-si, Gyeonggi-do (KR); Industry-Academic Cooperation Foundation, Yonsei University, Seoul (KR)

( * ) Notice: Subject to any disclaimer, the term of this patent is extended or adjusted under 35 U.S.C. 154(b) by 213 days.

(21) Appl. No.: 15/251,553

(22) Filed: Aug. 30, 2016

(65) Prior Publication Data
US 2017/0108476 A1    Apr. 20, 2017

(30) Foreign Application Priority Data

Oct. 20, 2015  (KR) .......................... 10-2015-0145888

(51) Int. Cl.
*G01N 30/64* (2006.01)
*G01N 30/96* (2006.01)
*B01J 20/281* (2006.01)

(52) U.S. Cl.
CPC .............. *G01N 30/64* (2013.01); *G01N 30/48* (2013.01); *G01N 30/96* (2013.01)

(58) Field of Classification Search
CPC ............................... G01N 30/48; G01N 30/64
See application file for complete search history.

(56) References Cited

U.S. PATENT DOCUMENTS 6,781,389 B1 * 8/2004 Colvin ................... G01N 27/07
                                                              324/449
8,653,449 B2    2/2014 Denton et al.
(Continued)

FOREIGN PATENT DOCUMENTS

JP    2009-289560 A    12/2009
JP    2011-013044 A     1/2011
(Continued)

Primary Examiner — Clayton E Laballe
Assistant Examiner — Jas Sanghera
(74) Attorney, Agent, or Firm — Lee & Morse, P.C.

(57) ABSTRACT

A conductivity detector includes a flow channel, an electrode arrangement, and a detector. The flow channel has a tube shape with a channel diameter through which a solution including ion components flows. The electrode arrangement is on the flow channel and includes at least an anode and at least a cathode. The anode and cathode are spaced apart by an electrode gap less than or equal to the channel diameter. The detector is connected to the electrode arrangement to detect electrical conductivity of the ion components.

20 Claims, 4 Drawing Sheets

(56) References Cited

U.S. PATENT DOCUMENTS

| | | |
|---|---|---|
| 8,901,506 B2 | 12/2014 | Fukada |
| 2006/0186046 A1* | 8/2006 | Liu ........................ G01N 30/62 |
| | | 210/656 |
| 2009/0201035 A1 | 8/2009 | Kaltenbach et al. |
| 2009/0218238 A1 | 9/2009 | Dasgupta et al. |
| 2012/0068723 A1* | 3/2012 | Sullivan ................ G01N 27/07 |
| | | 324/654 |

FOREIGN PATENT DOCUMENTS

| | | |
|---|---|---|
| JP | 2013-015482 A | 1/2013 |
| JP | 2014-055892 A | 3/2014 |
| KR | 10-2009-0128211 A | 12/2009 |
| KR | 10-2010-0126716 A | 12/2010 |
| KR | 10-2014-0076936 A | 6/2014 |

\* cited by examiner

CONDUCTIVITY DETECTOR AND ION CHROMATOGRAPHY SYSTEM INCLUDING THE SAME

CROSS-REFERENCE TO RELATED APPLICATION

Korean Patent Application No. 10-2015-0145888, filed on Oct. 20, 2015, and entitled, "Conductivity Detector and Ion Chromatography System Including the Same," is incorporated by reference herein in its entirety.

BACKGROUND

1. Field

One or more embodiments described herein relate to a conductivity detector and an ion chromatography system including a conductivity detector.

2. Description of the Related Art

Ultra pure water (UPW) has been used in various manufacturing processes for semiconductor devices. When using UPW, the ion concentration of impurities has been a focus and thus is often subject to careful monitoring, especially during the fabrication of highly integrated semiconductor devices of small size.

One approach for UPW monitoring involves performing a component analysis using ion chromatography. Ion chromatography may be performed by separating ionic components in the UPW in a separation column. The electrical conductivity of each ionic component is then detected by a conductivity detector. Qualitative and quantitative analyses are then performed based on the detected electrical conductivity for each ionic component.

A conductivity detector may detect ion components from UPW in a maximal concentration degree of parts per billion (ppb). Thus, detection of ion components from UPW, having a concentration below a certain degree of ppb or in a degree of parts per trillion (ppt), may not be accurate. When the concentration of UPW is excessively small (e.g., below a certain level of ppb), a larger UPW sample may be provided to the conductivity detector in an attempt to increase detection accuracy. However, providing a larger UPW sample increases the time and cost of performing conductivity detection.

SUMMARY

In accordance with one or more embodiments, a conductivity detector includes a flow channel having a tube shape with a channel diameter through which a solution including ion components flows; an electrode arrangement on the flow channel, the electrode arrangement including at least an anode and at least a cathode spaced apart by an electrode gap less than or equal to the channel diameter; and a detector connected to the electrode arrangement to detect electrical conductivity of the ion components.

The flow channel may include an inlet enclosed by the anode and into which the solution flows; an outlet enclosed by the cathode and out of which the solution flows; and a flow cell between the inlet and the outlet and across which the solution passes to provide an ion flow from the inlet to the outlet. The electrode gap may be substantially 0.3 to 1.0 times the channel diameter. The inlet, the outlet, and the flow cell may have substantially a same diameter, such that the flow channel has a uniform channel diameter along a flow path of the ion flow.

The detector may amplify the electrical conductivity by an amplification constant based on the following equation:

$$k = \frac{\left(\frac{D}{D_{ref}}\right)^2}{\frac{d}{d_{ref}}} = \frac{\gamma_D^2}{\gamma_d}$$

where k denotes the amplification constant, D denotes the channel diameter of the flow channel, $D_{ref}$ denotes a reference diameter of the flow channel, d denotes the electrical distance, $\gamma_d$ denotes a reduction ratio of the electrode gap and $\gamma_D$ denotes an increase ratio of the channel diameter.

Each of the inlet and the outlet may have a first diameter, and the flow cell may have a second diameter greater than the first diameter such that the flow cell has a volume greater than those of the inlet and the outlet. The electrode gap may be substantially in a range of 0.3 mm to 0.8 mm, and the channel diameter may be substantially in a range of 0.5 mm to 0.8 mm.

The conductivity detector may include an insulator between the anode and the cathode, wherein the insulator has a tube shape enclosing the flow channel. The conductivity detector may include a supplementary electrode to reduce polarization at the electrode. The supplementary electrode may include a first electrode on the flow channel and spaced from the anode, and a second electrode on the flow channel and spaced from the cathode.

The ion components in the solution may include one of positive ions or negative ions, and the solution may include an aqueous solution in which traces of the ion components are dissolved. The positive ion may include one of a lithium ion ($Li^+$), a sodium ion ($Na^+$), a potassium ion ($K^+$), or an ammonium ion ($NH4^+$), and the negative ion may include one of a fluorine ion ($F^-$), a chlorine ion ($Cl^-$), a bromide ion ($Br^-$), a nitrite ion ($NO2^-$), a nitrate ion ($NO3^-$), a phosphate ion ($PO4^{3-}$), a sulfate ion ($SO4^{2-}$), a carboxyl group ($COOH^-$), or an organic acid.

In accordance with one or more other embodiments, an ion chromatography system includes a sample supplier to supply a sample solution into a flow of an eluent that is a moving phase of an ion chromatography, to thereby generate a multi-component solution in which a plurality of ion components of a type is dissolved; a separation column to sequentially separate the ion components from the multi-component solution to generate a single component solution having a single type of the ion components and to sequentially discharge a plurality of the single component solutions in a time order; and a conductivity detector to detect a concentration of the ion components in the single component solution based on an electrical conductivity of the ion components.

The conductivity detector includes a flow channel having a tube shape with a channel diameter through which the single component solution flows, an electrode arrangement on the flow channel and including at least an anode and at least a cathode spaced apart by an electrode gap less than or equal to the channel diameter, and a detector connected to the electrode arrangement to detect the electrical conductivity of the ion components in the single component solution.

The ion chromatography system may include an eluent supplier having an eluent reservoir to store the eluent, and a delivery pump to deliver the eluent from the eluent reservoir through the separation column and the conductivity detector.

The sample supplier may include a sample dispenser to provide a fixed analysis quantity of the sample solution to a sample loop at a constant speed, and an auto injector to automatically inject the sample solution of the sample loop to an eluent flow path.

The separation column may include an ion exchange resin that is a stationary phase of the ion chromatography, the ion components in the multi-component solution sequentially separated according to a bonding strength between each of the ion components and a resin of the ion exchange resin.

The flow channel may include an inlet enclosed by the anode and connected to the separation column into which the single component solution flows in, an outlet enclosed by the cathode and out through which the single component solution flows, and a flow cell between the inlet and the outlet and across which the single component solution passes to provide an ion flow from the inlet to the outlet. The inlet, the outlet, and the flow cell may have substantially a same diameter, such that the flow channel has a uniform channel diameter along the ion flow. Each of the inlet and the outlet may have a first diameter, and the flow cell may have a second diameter greater than the first diameter such that the flow cell has a volume greater than the inlet and the outlet.

The ion chromatography system may include a suppressor between the separation column and the conductivity detector to remove noise ions having a polarity opposite to the ion components of the single component solution, the suppressor to remove noise from a signal of the electrical conductivity of the ion components in the single component solution.

In accordance with one or more other embodiments, a detector includes a channel; a first electrode on the channel; and a second electrode on the channel, wherein the channel is to carry a solution including ion components, wherein a gap between the first and second electrodes is less than or equal to a cross-sectional size of the channel, and wherein the first and second electrodes are to produce a detection signal indicative of a conductivity of the ion components, a detection accuracy of the detector based on the gap between the first and second electrodes and the cross-sectional size of the channel. Changing at least one of the gap or the cross-sectional size may change the electrical conductivity of the ion components. The cross-sectional size of the channel may be substantially uniform from an inlet to an outlet of the channel. The cross-section size may be a diameter of the channel. The gap between the first and second electrodes may be less than the cross-sectional size of the channel.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
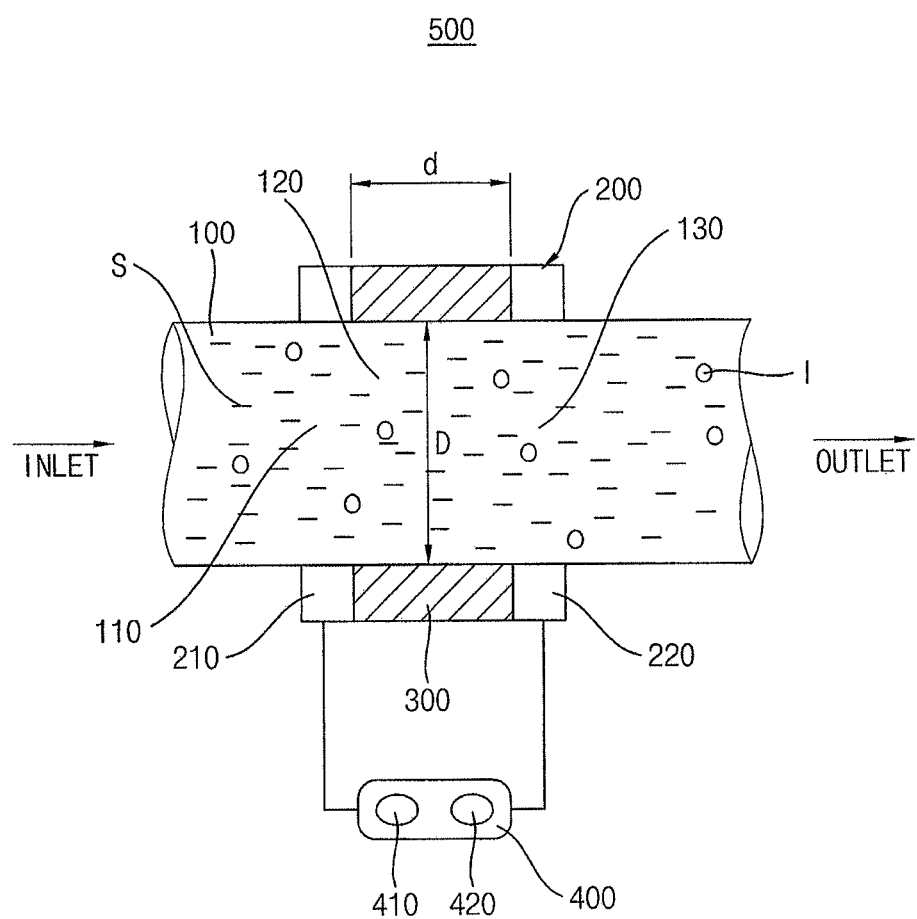
FIG. 1 illustrates an embodiment of a conductivity detector.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. The embodiments may be combined to form additional embodiments.

In the drawings, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein FIG. 1 illustrates an embodiment of a conductivity detector 500, which, for example, may detect a small amount of ion components in a solution. Referring to FIG. 1, conductivity detector 500 may include a flow channel 100, an electrode arrangement 200, and a detecting unit 400. The flow channel 100 has a tube shape with a channel diameter D for carrying a solution S with ion components I. The electrode arrangement 200 is on an outer surface of the flow channel 100 and has at least an anode 210 and at least a cathode 220 spaced apart by an electrode gap d that is less than the channel diameter D. The detecting unit 400 is connected to the electrode arrangement 200 for detects electrical conductivity of the ion components I.

The flow channel 100 may provide a flow path for the solution S having ion components I, and the ion components I passing through the flow path may be detected as an electrical signal proportional to the concentration of the ion components I in the solution S. Thus, the electrical conductivity and the concentration of ion components I may be determined based on electrical signal. Various materials may be used to form the flow channel 100 as long as the flow channel 100 have sufficient conductivity for detecting the electrical signal and sufficient etching resistivity with respect to the solution including the ion components I.

The flow channel 100 may include an inlet 110 enclosed by the anode 210 and into which the solution S flows, an outlet 130 enclosed by the cathode 220 through which the solution S flows, and a flow cell 120 between the inlet 110 and the outlet 130 and across which the solution S passes and thereby providing ion flow from the inlet 110 to the outlet 130.

The solution may include an aqueous solution, in which a small quantity or traces of the ion components I may be dissolved in ultra pure water (UPW) at a concentration below a degree of parts per billion (ppb) or in the degree of parts per trillion (ppt). For example, the ion components in the solution S may include one of positive ions or negative ions. Examples of positive ions include lithium ion ($Li^+$), a natrium ion ($Na^+$), a potassium ion ($K^+$), an ammonium ion ($NH4^+$), and combinations thereof. Examples of negative ions include fluorine ion ($F^-$), a chlorine ion ($Cl^-$), a bromide ion ($Br^-$), a nitrite ion ($NO2^-$), a nitrate ion ($NO3^-$), a phosphate ion ($PO4^{3-}$), a sulfate ion ($SO4^{2-}$), a carboxyl group (COOH), an organic acid, and combinations thereof.

In the present example embodiment, the flow channel 100 may be an open system in which the solution S may flow through the flow cell 120 substantially in a steady state steady flow (SSSF).

For example, the inlet 110 may be connected to a separation column in which a plurality of ion components of a certain type may be individually and sequentially separated. Thus, a solution having a single type of ion components may flow into the flow cell 120 through the inlet 110. The solution may flow out from the flow cell 120 through the outlet 130 and into, for example, a waste tank, another separation column, or another analysis apparatus. When the solution has multiple types of ion components, the solution may flow again into the flow cell 120 through the inlet 110 in a predetermined time interval to separate another type of ion components. In one example embodiment, the inlet 110, the flow cell 120, and the outlet 130 may have the same diameter, so the flow channel 100 may have a uniform channel diameter D along a flow path of the solution.

The electrode arrangement 200 may be arranged on an outer surface of the flow channel 100. The anode 210 and the cathode 220 of the electrode arrangement 200 may be spaced apart by an electrode gap d less than the channel diameter D. The electrode arrangement 200 may have, for example, a ring shape enclosing the tube shaped flow channel 100. Thus, the flow channel 100 may penetrate through the ring-shaped electrode arrangement 200.

In one example embodiment, the outer surface of the inlet 110 may be enclosed by the anode 210 and the outer surface of the outlet 130 may be enclosed by the cathode 220. As a result, the flow cell 120 may be interposed between the anode 210 and the cathode 220. The flow cell 120 may have, for example, a disk shape with a channel diameter D greater than the electrode gap d. The width of the flow cell 120 may correspond, for example, to the electrode gap d.

The flow cell 120 may be enclosed by an insulator 300 between the anode 210 and the cathode 220. Thus, the anode 210 and the cathode 220 may be electrically separated from each other and the flow cell 120 may be protected from surroundings.

The insulator may include, for example, one of polyether ether ketone (PEEK) and polytetra fluoro ethylene (PTFE). The electrode may include, for example, one of stainless steel and platinum (Pt).

Since the anode 210 and the cathode 220 are separated by the insulator 300 and are arranged at respective ends of the flow cell 120, the flow of ion components I through the flow cell 120 may be detected as an electrical current. The detecting unit 400 may be connected to the anode 210 and the cathode 220 to detect an electrical voltage between the inlet 110 and the outlet 130. Thereafter, the detecting unit 400 may analyze the electrical signal to determine the electrical conductivity and concentration of the ion components I in the solution S.

In an example embodiment, the detecting unit 400 may include a power source 410 for applying electrical power to the electrode arrangement 200 and a measuring instrument 420 for detecting a voltage and current intensity between the anode 210 and the cathode 220.

The measuring instrument 420 may include, for example, a nano voltmeter and/or a nano ampere meter having a wheatstone bridge or an amplifying circuit. The measuring instrument 420 may include, for example, a temperature compensation circuit for converting the detected electrical conductivity of the ion components I to a standard conductivity at a temperature of about 25° C. The measuring instrument 420 may have a configuration based on the structure of the electrode arrangement 200 and the flow channel 100.

When electrical power is applied to the electrode arrangement 200, the electrical conductivity of ion components I may be detected by the detecting unit 400 according to the Equation 1.

$$C = \frac{L}{K_c} \quad (1)$$

where C denotes electrical conductivity, L denotes a specific conductivity of the ion component, and $K_c$ denotes a cell constant of the conductivity detector 500.

Since the solution S flows through the flow cell 120 enclosed by the electrode arrangement 200, the anode 210, the flow cell 120, and the cathode 220 may function as a single electrode of a virtual electrical circuit connected to the detecting unit 400. Thus, ion components I may penetrate through a cross-sectional area of the flow channel 100 and may travel the distance between the anode 210 and the cathode 220. For example, the ion components I in the solution S may move along the flow cell 120 a distance corresponding to the electrode gap d.

Therefore, the cell constant $K_c$ may be expressed by Equation 2.

$$K_c = \frac{l}{A} = \frac{4d}{\pi D^2} \quad (2)$$

where A denotes the cross-sectional area through which the solution S flows and thus the ion components I flow and l denotes the gap between the anode and cathode.

The electrical conductivity of the ion components I may be obtained according to Equation 3, which is based on Equations 1 and 2.

$$C = L\frac{\pi D^2}{4d} = \frac{\pi L}{4}\frac{D^2}{d} \quad (3)$$

Thus, the electrical conductivity C of ion components I in the solution S may be proportional to a form factor of the conductivity detector 500 determined by the channel diameter D of the flow channel 100 and the electrode gap d between the anode 210 and the cathode 220. The electrical conductivity C of the ion components I may therefore be amplified just by varying the form factor of the conductivity detector 500, and the form factor of the conductivity detector 500 may be varied just by changing the channel diameter D and the electrode gap d.

A conductivity ratio k of the electrical conductivity C, detected in accordance with the present example embodiment of the conductivity detector 500 with respect to that of a reference electrical conductivity $C_{ref}$ detected by another type of conductivity detector, may be expressed by Equation 4.

$$\frac{C}{C_{ref}} = \frac{d_{ref}}{d_{ref}^2}\frac{D}{d} = \frac{d_{ref}}{d}\left(\frac{D}{D_{ref}}\right)^2 = k \quad (4)$$

When the conductivity ratio k is over 1, the electrical conductivity C may be amplified more than the reference electrical conductivity $C_{ref}$. The other conductivity detector may include a reference flow channel having a reference channel diameter $D_{ref}$, and the anode and the cathode may be spaced apart on the reference flow channel by a reference gap $d_{ref}$. Therefore, the conductivity ratio k in Equation 4 may indicate an amplification constant that determines the magnitude of a signal amplification of the electrical conductivity due to modification of the shape or form of the conductivity detector 500. For that reason, the conductivity ratio k may also be referred to as the amplification constant for convenience.

Thus, the amplification constant k may be proportional to a reduction ratio $\gamma_d$ of an electrode gap and an increase ratio $\gamma_D$ of the channel diameter in the conductivity detector 500, as indicated in Equation 5.

$$k = \frac{\left(\frac{D}{D_{ref}}\right)^2}{\frac{d}{d_{ref}}} = \frac{\gamma_D^2}{\gamma_d} \quad (5)$$

Therefore, a decrease in the electrode gap d and an increase in the channel diameter D may lead to an increase of the amplification constant k. Thus, since the amplification constant k is inversely proportional to the reduction ratio $\gamma_d$ of the electrode gap d and proportional to a square of the increase ratio $\gamma_D$ of the channel diameter D, electrical conductivity may be sufficiently detected just by a proper combination of the reduction ratio $\gamma_d$ and the increase ratio $\gamma_D$, no matter how small the amount of ion components may be in the solution S. Accordingly, the impurity ions in ultra pure water (UPW) may be sufficiently detected by the conductivity detector 500, even though the concentration of the impurity ions may be under a degree of ppb or ppt.

Changing the channel diameter D may require the flow channel 100 to be exchanged for another flow channel and may also require relatively high maintenance costs of the conductivity detector 500. However, changing the electrode gap d may just require a modification in the location of the anode 210 and/or the cathode 220 on the flow channel 100 and thus involves relatively low maintenance costs of the conductivity detector 500.

For these reasons, the amplification constant k may be controlled just by varying the electrode gap d, which may be accomplished without changing the channel diameter D of the flow channel 100 in accordance with the present example embodiment. For example, when the electrode gap d is reduced to about 80% of the reference gap $d_{ref}$, and thus the reduction ratio $\gamma_d$ of an electrode gap may be about 20%, the electrical conductivity C may be amplified to about 1.25 times the reference electrical conductivity $C_{ref}$. Thus, the amplification constant k may be controlled to be 1.25 just by varying the reduction ratio $\gamma_d$ as much as about 0.2. However, the amplification constant k may be more accurately controlled by varying the increase ratio $\gamma_D$ of the channel diameter D together with the reduction ratio $\gamma_d$.

In one example embodiment, the electrode gap d may be controlled to be less than the channel diameter D of the flow channel 100, so that the conductivity detector 500 may have a disk shape. While other types of conductivity detectors are shaped into a cylinder, with the reference electrode gap larger than the reference channel diameter, the electrode gap d may be controlled to be less than or maximally equal to the channel diameter D in the conductivity detector 500, thereby sufficiently amplifying the electrical conductivity C.

For example, the electrode gap d may be about 0.3 times to about 1.0 times the channel diameter D, and more particularly about 0.4 times to about 0.6 times the channel diameter D. In the present example embodiment, the channel diameter D may be in a range of about 0.5 mm to about 0.8 mm and the electrode gap d may be in a range of about 0.3 mm to about 0.8 mm. When the flow channel 100 has a channel diameter D of about 0.5 mm, the electrode gap d may be controlled to about 0.3 mm to about 0.5 mm. Thus, the conductivity detector 500 may have a disk shape. In addition, when the flow channel 100 is substituted with a new flow channel having the channel diameter D of about 0.8 mm, the electrode gap d may also be controlled to about 0.3 mm to about 0.8 mm, to thereby provide a disk-shaped conductivity detector 500 in spite of exchange of the flow channel 100.

While the present example embodiment discloses that the channel diameter D may be varied in a range of about 0.5 mm to about 0.8 mm and the electrode gap d may be varied in a range of about 0.3 mm to about 0.8 mm, any other variation ranges of the channel diameter D and the electrode gap d may be allowable as long as the channel diameter D and the electrode gap d sufficiently satisfy Equation 5 with respect to the expected amplification constant in view of configuration and operation requirements of the conductivity detector 500.

Therefore, the electrical conductivity of the ion components I in the solution S may be accurately detected without any amount increase of the solution S by the conductivity detector 500, irrespective of how small the concentration of ion components I is in the solution S. Thus, the impurity ions in ultra pure water (UPW) having a concentration may under ppb or ppb may be sufficiently detected by the conductivity detector 500 just by varying the locations of the anode 210 and the cathode 220, without increasing the amount of UPW to be supplied.

Figure 2:
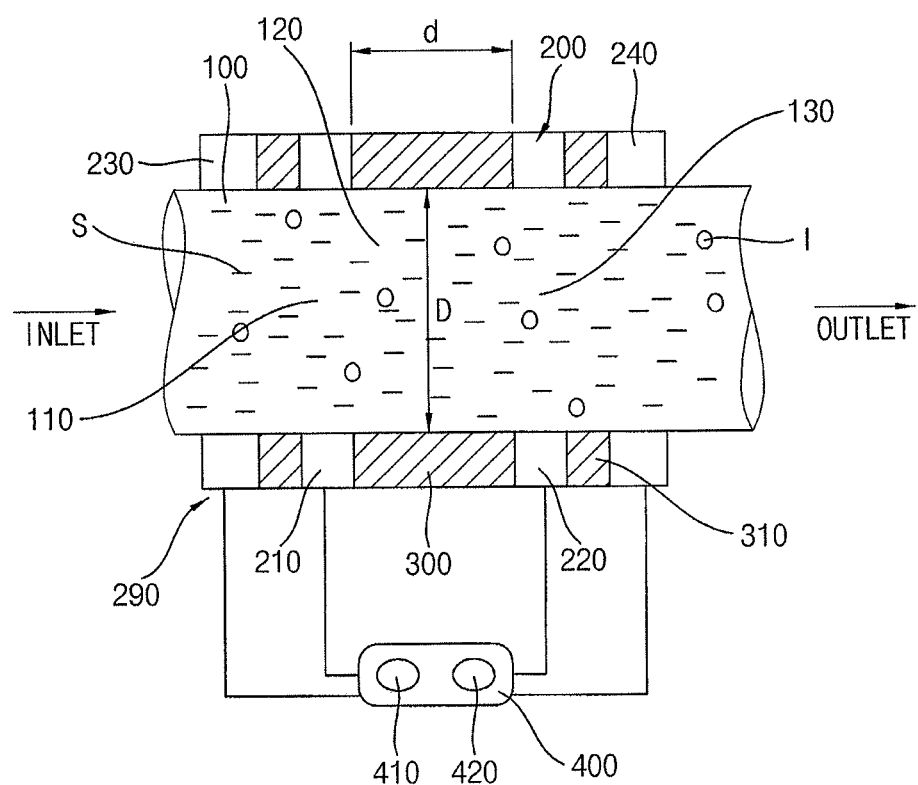
FIG. 2 illustrates another embodiment of a conductivity detector.

FIG. 2 illustrates another embodiment of a conductivity detector 501 which has substantially the same structure as the conductivity detector 500 in FIG. 1, except for a supplementary electrode on the flow channel.

Referring to FIG. 2, the conductivity detector 501 includes a supplementary electrode 290 for reducing or minimizing a polarization at the electrode arrangement 200. For example, the supplementary electrode 290 may include a first electrode 230 on the outer surface of the flow channel 100 and spaced apart from the anode 210 and a second electrode 240 on the outer surface of the flow channel 100 and spaced apart from the cathode 220. An additional insulator 310 may be between the first electrode 230 and the anode 210 and between the second electrode 240 and the cathode 220. Thus, the first electrode 230 and the anode 210 may be electrically separated from each other, and the second electrode 240 and the cathode 220 may be electrically separated from each other by the additional insulator 310.

The supplementary electrode 290 may have a ring shape enclosing the flow channel 100. The flow channel 100 may also penetrate through the ring-shaped supplementary electrode 290. In the present example embodiment, the electrode arrangement 200, the insulator 300, the supplementary electrode 290, and the additional insulator 310 may be configured into a single ring structure through which the flow channel 100 may penetrate.

When electrical power is applied to the electrode arrangement 200, polarizations and oxidation-reduction reactions may be carried out at a boundary surface between the solution S and the electrode arrangement 200. As a result, a plurality of bubbles may be generated on the surface of the electrode arrangement 200. The bubbles on the electrode arrangement 200 may restrict current flow between the flow channel 100 and the electrode arrangement 200, thereby reducing the detecting efficiency of the detecting unit 400.

In the conductivity detector 501, electrical power may be applied to the first and the second electrodes 230 and 240 in place of the anode 210 and the cathode 220, and the detecting unit 400 may still detect the electrical voltage and/or the electrical current between the anode 210 and the cathode 220. Thus, no bubbles may be formed between the electrode arrangement 200 and the solution S, and electrical conductivity may be accurately detected without any detection interrupts from the polarization. Thus, a small quantity of ion components I in the solution S (such as impurity ions in the UPW) may be accurately detected with sufficiently high accuracy.

Figure 3:
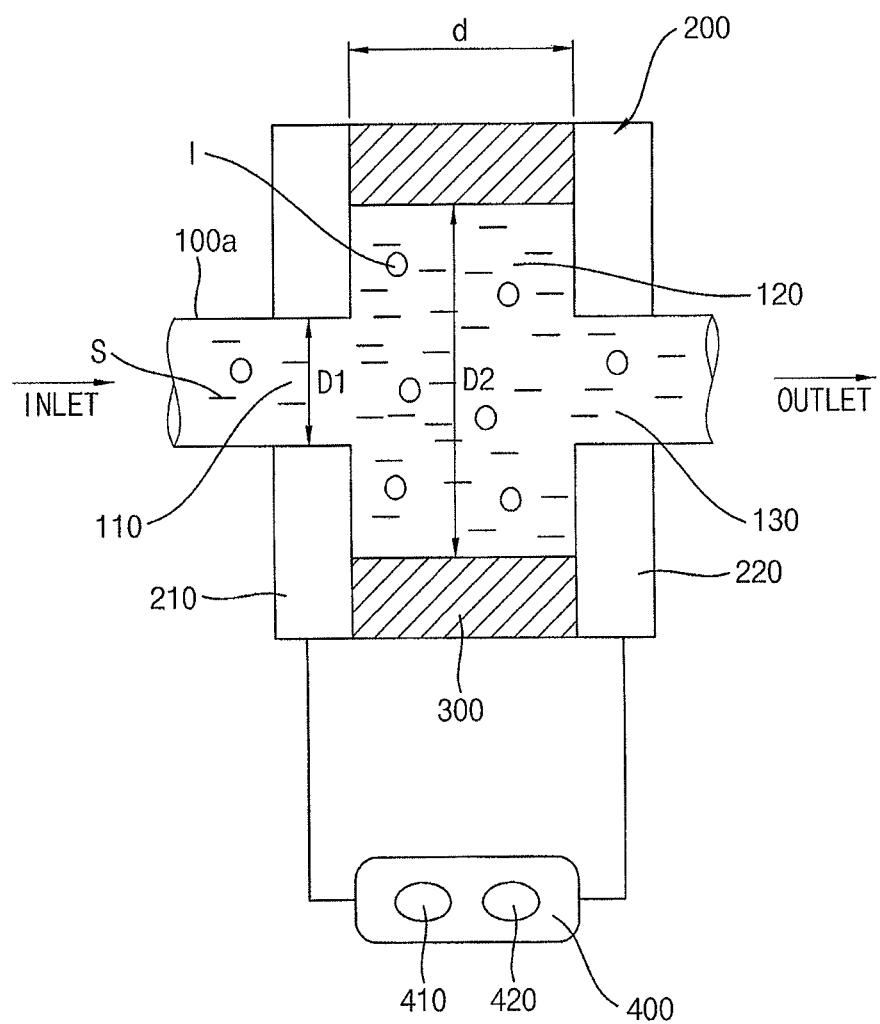
FIG. 3 illustrates another embodiment of a conductivity detector.

FIG. 3 illustrates another embodiment of a conductivity detector 502 which has the same structure as the conductivity detector 500 in FIG. 1, except that the size of the flow cell 120 is different from those of the inlet 110 and the outlet 130.

Referring to FIG. 3, the conductivity detector 502 includes a modified flow channel 100a in which the flow cell 120 has a volume larger than those of the inlet 110 and the outlet 130. For example, the inlet 110 and the outlet 130 may have a tube shape with a first channel diameter D1. The flow cell 120 may have a tube shape connected to the inlet 110 and the outlet 130 and a second channel diameter D2 greater than the first channel diameter D1.

The flow speed may decrease in the flow cell 120 when the solution S flows into the flow cell 120 and may increase when the solution S flows out from the flow cell 120 through the outlet 130. Thus, the number of ion components I in the flow cell 120 may increase when the solution S penetrates through the conductivity detector 502. Since the anode 210, the flow cell 120, and the cathode 220 may be provided as a single electrode and the flow speed of the solution S may decrease in the flow cell 120 due to volume expansion, the average number of ion components I in the solution S may increase compared with the flow channel 100 of the conductivity detector 500 in FIG. 1 when the ion components I are uniformly solved in the solution S.

Thus, the detection limit of the detecting unit 400 may be improved in accordance with an increase in the number of ion components I in the flow cell 120. The number of ion components I in the flow cell 120 may be determined by the volume expansion of the flow cell 120, and the volume expansion of the flow cell 120 may be varied based on the diameter ratio of the first and the second channel diameters D1 and D2. Accordingly, the detection limit may be easily improved in the conductivity detector 502 just by controlling the diameter ratio of the first and the second channel diameters D1 and D2.

In the present example embodiment, the first channel diameter D1 may be in a range of about 50% to 70% of the second channel diameter D2.

While ion components are dissolved in the aqueous solution (such as impurity ions in UPW) in the present embodiment, other solvents may also be used for detecting the electrical conductivity of traces of ion components in the solvent in view of electrical characteristics between the ion components and the solvent.

According to the example embodiments of the conductivity detector, the conductivity detector may be modified into a disk shape, in which the electrical gap between the anode and the cathode may be less than the channel diameter of the flow channel. As a result, the detection limit may be improved without design changes or instrumental modification thereof. For example, electrical conductivity may be sufficiently detected with high accuracy just by changing the form factor of the conductivity detector, irrespective of how small the amount of ion components I may be in the solution S. Accordingly, the impurity ions in ultra pure water (UPW) may be sufficiently detected by the conductivity detector 500, even though the concentration of the impurity ions may be under a degree of ppb or ppt.

Figure 4:
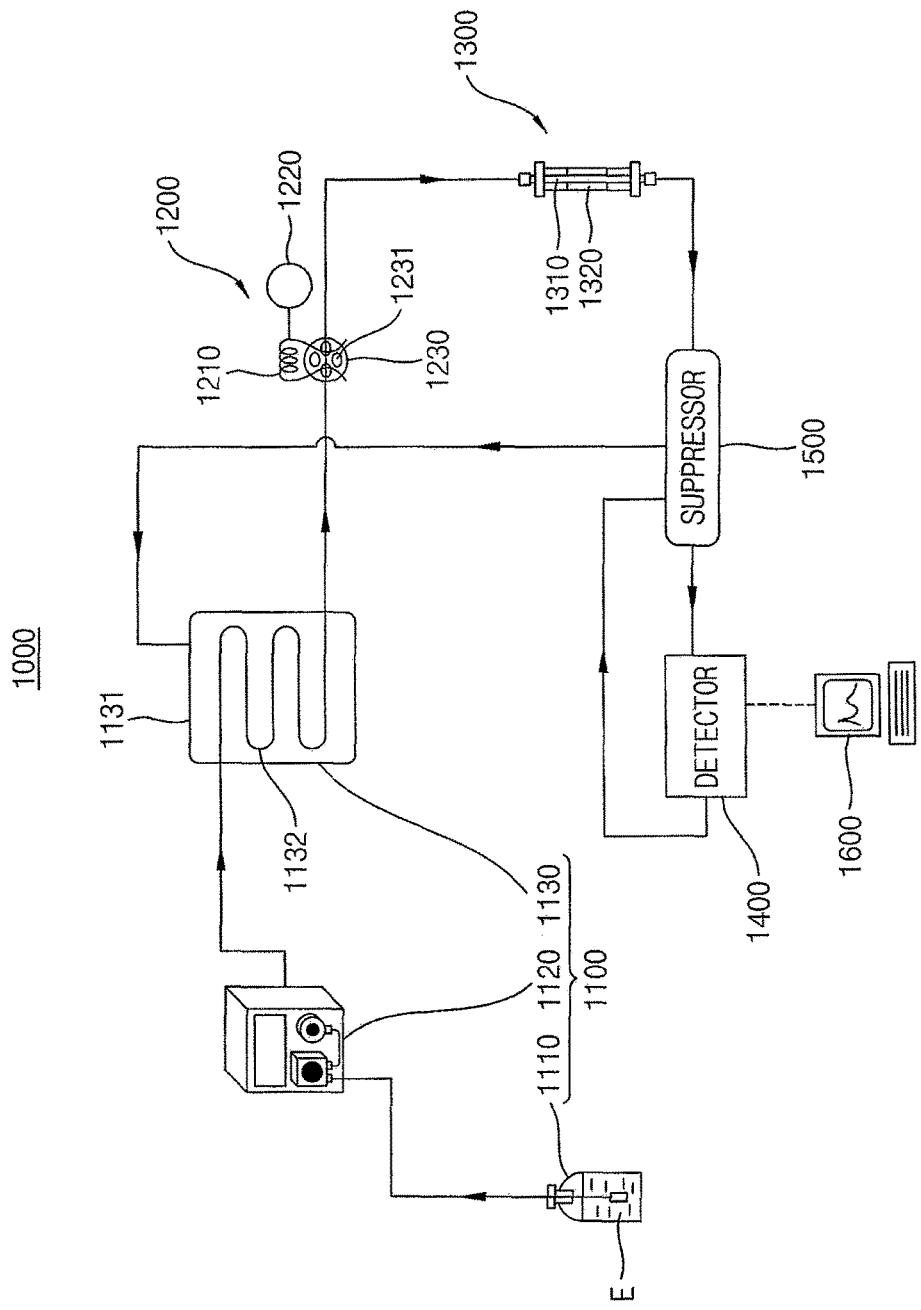
FIG. 4 illustrates an embodiment of an ion chromatography system.

FIG. 4 illustrates an embodiment of an ion chromatography system 1000, which may include an eluent supplier 1100, a sample supplier 1200, a separation column 1300, and a conductivity detector 1400. The eluent supplier 1100 supplies an eluent E that may be a moving phase of an ion chromatography. The sample supplier 1200 supplies a sample solution into a flow of the eluent E, thereby generating a multi-component solution in which a plurality type of ion components may be dissolved. The separation column 1300 sequentially separates the ion components from the mixed solution to thereby generate a single component solution having a single type of ion components and sequentially discharges a plurality of the single component solutions in a time order. The conductivity detector 1400 detects a concentration of the ion components in the single component solution based on an electrical conductivity of the ion components.

For example, the eluent supplier may include an eluent reservoir 1110 storing the eluent E, a delivery pump 1120 delivering the eluent E via the separation column 1300 and the conductivity detector 1400 from the eluent reservoir 1110, and a degassing member 1130 for reducing or minimizing damping characteristics of the eluent E in the separation column 1300.

The eluent E may function as a moving phase of an ion chromatography, so that a plurality of ion components may be solved into the eluent E from the sample solution. Thus, the eluent E and the sample solution may be mixed into the multi-component solution in which a plurality of ion components of a certain type may be dissolved in the ion chromatography system 1000. The eluent E may have low viscosity for good fluidity in the ion chromatography system 1000 and high dissolubility to the solutes of the sample solution. For example, the eluent E may have high chemical stability with respect to a base material of the separation column that may function as a stationary phase of the ion chromatography.

One or more additives may be supplied to the UPW for increasing the dissolubility and miscibility with respect to an analysis specimen. In addition, a buffer solution may be added to the UPW for separating ionic components from the analysis specimen.

The delivery pump 1120 may generate a pressure for delivering the eluent E from the eluent reservoir 1110 through the separation column 1300 and the conductivity detector 1400, so that the eluent E may sufficiently reach the conductivity detector 1400 from the eluent reservoir 1110. The eluent E may move, for example, at a constant speed in the ion chromatography system 1000 by the deliver pressure.

The degassing member 1130 may include a membrane tube 1132 arranged in a vacuum chamber 1131 and connected to the delivery pump 1120. The eluent E including gas components may flow into the membrane tube 1132 in the vacuum chamber 1131. The gas components may be removed from the eluent E into the vacuum chamber 1131 by the vacuum pressure. Thus, gases components in the eluent E may be reduced or minimized by the degassing member 1130, thereby reducing or minimizing the damping characteristics of the eluent E in the separation column 1300.

While the present example embodiment discloses that the degassing member 1130 is arranged between the delivery pump 1120 and the sample supplier 1200, the degassing member 1130 may be between the eluent reservoir 1110 and the delivery pump 1120 in at least one example embodiment.

The sample supplier 1200 may include a sample loop 1210 holding a sample solution, a sample dispenser 1220 providing a fixed quantity of the sample solution to the sample loop 1210 at a constant speed, and an auto injector 1230 automatically injecting the sample solution of the sample loop 1210 to a flow path of the eluent E. For example, the sample dispenser 1220 may include a peristaltic pump, and the auto injector 1230 may include a plurality of holding ports 1231 and a multiport valve system in which the sample solution in the sample loop 1210 may be supplied to the eluent E just by changing the holding port 1231.

In the present example embodiment, the sample solution may include an ultra pure water (UPW) having an electrical resistance more than about 18MΩ. For example, when the sample solution includes UPW in which a plurality of impurity ions are dissolved and water or an aqueous solution is used for the moving phase of the ion chromatography system 1000, no eluent supplier may be provided with the ion chromatography system 1000. In such a case, the UPW may be supplied to the ion chromatography system 1000 for detecting the concentration of the impurity ions in the UPW by the sample supplier 1200 with comparatively fewer elements.

For example, when the sample solution including one or more solvents for semiconductor manufacturing processes such as UPW is supplied to a sample reservoir for detecting the impurity ions therein, the sample dispenser 1220 may extract a fixed analysis quantity of the sample solution from the sample reservoir and may provide the fixed analysis quantity into the sample loop 1210. Then, the extracted sample solution may be supplied to the holding port 1231 of the auto injector 1230 from the sample loop 1210, and the auto injector 1230 may linearly move or rotate by a predetermined unit in such a way that the holding port 1231 in which an analysis quantity of the sample solution may be hold may be aligned with the flow path of the eluent E. Thereafter, the port valve of the holding port 1231 may be open and the sample solution may be mixed with the eluent E.

Thus, the sample solution and the eluent E may be mixed into the multi-component solution in which a plurality of ion components of a certain type may be dissolved. For example, various ion components in the sample solution may be mixed with the eluent E, and the multi-component mixed solution may be supplied to the separation column 1300.

A plurality of the holding ports 1231 having different holding volumes may be provided with the auto injector 1230, and the analysis quantity of the sample solution may be varied in view of the concentration degree of the ion components in the sample solution. In the present example embodiment, 10 holding ports 1231 may be provided with the auto injector 1230.

After mixing of the sample solution with the eluent E has been completed, the multi-component mixed solution may be supplied to the separation column 1300. The ion components may be sequentially separated, one by one, in accordance with an ionic bond of each ion component and the stationary phase materials in the separation column 1300. For example, the separation column 1300 may include an ion exchange resin 1310 arranged in a tube-shaped housing as the stationary phase of the ion chromatography, and a temperature controller 1320 for controlling the temperature of the solution in the separation column 1300 to be uniform.

The ion exchange resin 1310 may be fixed into the housing and may be physically and chemically stable to the eluent E passing through the separation column 1300. Thus, the ion exchange resin 1310 may function as the stationary phase of the ion chromatography, while the eluent E may function as the moving phase of the ion chromatography.

When the multi-component solution reaches the ion exchange resin 1310 in an equilibrium state with ions of the eluent E, the chemical equilibrium state in the ion exchange resin 1310 may be broken and the ion components in the multi-component solution may bond to the resin of the ion exchange resin 1310.

Since the eluent E may be continuously supplied to the separation column 1300 by the delivery pump 1120, bonding of the ion components and resin of the ion exchange resin 1310 may be sequentially broken in accordance with the bonding strength of each ion component to the stationary phase resin. Thus, the stronger the bonding strength of the ion component is, the longer the ion component stays in the separation column 1300. Thus, a retention time (or a stay time) of each ion component in the separation column 1300 may vary according to the bonding strength, and each ion component may be individually discharged from the separation column 1300 as the retention time may pass.

The separated ion components from the stationary phase resin of the ion exchange resin 1310 may still be dissolved in the eluent E and discharged from the separation column 1300. Thus, the multi-component solution may be changed into a single component solution, in which a single type ion components are dissolved, when discharging the separation column 1300. Thus, the single component solution may be sequentially discharged from the separation column 1300 in a time order according to the bonding strength of each ion component therein.

For example, the temperature controller 1320 may control an inner temperature of the separation column 1300 under a uniform temperature, so that the multi-component solution, the eluent E, and the single component solution flows through the separation column 1300 under the uniform temperature.

The conductivity detector 1400 may detect the electrical conductivity of the ion components in the single component solution, thereby obtaining the concentration of the ion components of the sample solution. The conductivity detector 1400 may have the same structure as any one of the conductivity detectors 500 to 502 in FIGS. 1 to 3.

For example, the conductivity detector 1400 may include a flow channel 100 having a tube shape and a channel diameter D through which the single component solution may flow, an electrode arrangement 200 on an outer surface of the flow channel 100 and having at least an anode 210 and at least a cathode 220 spaced apart by the electrode gap d less than the channel diameter D, and a detecting unit 400 connected to the electrode arrangement 200 for detecting electrical conductivity of the ion components in the single component solution.

The flow channel may include an inlet 110 enclosed by the anode 210 and connected to the separation column 1300, and into which the single component solution may flow in, an outlet 130 enclosed by the cathode 220 and through which the single component solution may flow out, and a flow cell 120 between the inlet 110 and the outlet 130 and across which the single component solution may pass, thereby providing ion flow from the inlet 110 to the outlet 130.

The inlet 110, the outlet 130, and the flow cell 120 may have the same diameter, so the flow channel 100 may have a uniform channel diameter D along the ion flow. The conductivity detector 1400 may have a disk shape in such a configuration that the electrode gap d between the anode 210 and the cathode 220 is less than the channel diameter D. Therefore, the cell constant Kc of the conductivity detector 1400 may be reduced just by varying the electrode gap and the channel diameter. Thus, the detected signal may be amplified by the amplification constant in the conductivity detector 1400. As a result, the conductivity detector 1400 may accurately detect the electrical conductivity of ion components, and the concentration of the ion components in the single component solution may be obtained from the detected conductivity. For example, impurity ions in UPW may be sufficiently detected by the conductivity detector 1400, even though the concentration of impurity ions may be under a degree of ppb or ppt due to a small cell constant Kc of the conductivity detector 1400.

As shown in FIG. 3, the inlet 110 and the outlet 130 may have a first diameter D1 and the flow cell 120 may have a second diameter D2 lager than the first diameter D1. Thus, the flow cell 120 may have a volume greater than those of the inlet 110 and the outlet 130. Thus, the number of ion components in the flow cell 120 may increase when the single component solution flows through the flow cell 120, thereby increasing the detection accuracy of the conductivity detector 1400.

In addition, the conductivity detector 1400 may include a supplementary electrode 290 for reducing or minimizing a polarization at the electrode arrangement 200. As shown in FIG. 2, the supplementary electrode 290 may include a first electrode 230 and a second electrode 240. The first electrode 230 is arranged on the outer surface of the flow channel 100 and spaced apart from the anode 210. The second electrode 240 is arranged on the outer surface of the flow channel 100 and spaced apart from the cathode 220. Thus, bubbles that otherwise might be caused by polarization of the single component solution do not occur between the electrode arrangement 200 and the single component solution.

For example, electrical power 410 may be applied to the supplementary electrode 290, not to the electrode arrangement 200. In this case, bubbles caused by polarization of the solution may be generated between the single component solution and the first and the second electrodes 230 and 240, and no bubbles may be generated at the anode 210 and the cathode 220. Therefore, electrical conductivity may be accurately detected without any detection interrupts. For example, a small quantity of ion components (such as impurity ions in UPW) may be accurately detected with sufficiently high accuracy.

The electrical conductivity or concentration of ion components may be categorized by each ion component and may be visually displayed on a display device by a system controller 1600.

In the present example embodiment, ion components may include positive ions or negative ions dissolved in UPW as impurity ions. Thus, the multi-component solution and the single component solution may include an aqueous solution in which the ion components may be dissolved. Examples of the positive ions include one of a lithium ion ($Li^+$), a sodium ion ($Na^+$), a potassium ion ($K^+$), an ammonium ion ($NH4^+$) and combinations thereof. Examples of negative ions may include one of a fluorine ion ($F^-$), a chlorine ion ($Cl^-$), a bromide ion ($Br^-$), a nitrite ion ($NO2^-$), a nitrate ion ($NO3^-$), a phosphate ion ($PO4^{3-}$), a sulfate ion ($SO4^{2-}$), a carboxyl group ($COOH^-$), an organic acid and combinations thereof.

The ion chromatography system 1000 may further include a suppressor 1500 between the separation column 1300 and the conductivity detector 1400 for removing noise ions having a polarity opposite to the ion component of the single component solution. As a result, noise signals may be removed from a signal corresponding to the electrical conductivity of the ion components in the single component solution.

When the ion components of the single component solution include positive ions and the suppressor 1500 substitutes the noise ions having negative polarity with hydroxyl ions ($OH^-$), noise signals may be removed from the signal corresponding to the electrical conductivity of the positive ion components in the single component solution. In contrast, when ion components of the single component solution include negative ions and the suppressor substitutes the noise ions having positive polarity with hydrogen ions ($H^+$), noise signals may be removed from the signal corresponding to the electrical conductivity of the negative ion components in the single component solution.

In accordance with one or more of the aforementioned embodiments, a conductivity detector has a disk shape and an electrical gap between an anode and a cathode of the detector may be less than the channel diameter of the flow channel. As a result, the cell constant Kc may be reduced and detection accuracy of the conductivity detector may be increased without design changes or instrumental modification thereof. Thus, electrical conductivity may be sufficiently detected with high accuracy just by changing the form factor of the conductivity detector, no matter how small the amount of ion components I is in the solution S. Accordingly, impurity ions in ultra pure water (UPW) may be sufficiently detected by the conductivity detector, even though the concentration of impurity ions may be under a degree of ppb or ppt.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, it will be understood by those of skill in the art that various changes in form and details may be made without departing from the spirit and scope of the embodiments set forth in the claims.

What is claimed is:

1. A conductivity detector, comprising:
  a flow channel having a tube shape with a channel diameter through which a solution including an ion component flows;
  an electrode arrangement on the flow channel, the electrode arrangement including an anode and a cathode spaced apart by an electrode gap less than or equal to the channel diameter; and
  a detector connected to the electrode arrangement to detect a voltage between the anode and the cathode corresponding to electrical conductivity of the ion component.

2. The conductivity detector as claimed in claim 1, wherein the flow channel includes:
  an inlet enclosed by the anode and into which the solution flows;
  an outlet enclosed by the cathode and out of which the solution flows; and
  a flow cell between the inlet and the outlet and through which the solution flows from the inlet to the outlet.

3. The conductivity detector as claimed in claim 2, wherein the inlet, the outlet, and the flow cell have substantially a same diameter, such that the flow channel has a uniform channel diameter from the inlet to the outlet.

4. The conductivity detector as claimed in claim 2, wherein:
  each of the inlet and the outlet has a first diameter, and
  the flow cell has a second diameter greater than the first diameter such that the flow cell has a diameter greater than those of the inlet and the outlet.

5. The conductivity detector as claimed in claim 1, wherein the detector is to amplify the electrical conductivity by an amplification constant based on the following equation:

$$k = \frac{\left(\frac{D}{D_{ref}}\right)^2}{\frac{d}{d_{ref}}}$$

where k denotes the amplification constant, D denotes the channel diameter of the flow channel, $D_{ref}$ denotes a reference diameter of a reference flow channel, d denotes the electrode gap between the anode and the cathode, and $d_{REF}$ denotes a reference gap between a reference anode and cathode of the reference flow channel.

6. The conductivity detector as claimed in claim 1, further comprising:
  an insulator between the anode and the cathode,
  wherein the insulator has a tube shape enclosing the flow channel.

7. The conductivity detector as claimed in claim 1, further comprising:
  a supplementary electrode to reduce polarization at the electrode arrangement.

8. The conductivity detector as claimed in claim 7, wherein the supplementary electrode includes:
  a first electrode on the flow channel and spaced from the anode, and
  a second electrode on the flow channel and spaced from the cathode.

9. The conductivity detector as claimed in claim 1, wherein:
  the ion component in the solution includes one of a positive ion or a negative ion, and
  the solution includes an aqueous solution in which the ion component is dissolved.

10. The conductivity detector as claimed in claim 9, wherein:
the positive ion includes one of a lithium ion, a sodium ion, a potassium ion, or an ammonium ion, and
the negative ion includes one of a fluorine ion, a chloride ion, a bromide ion, a nitrite ion, a nitrate ion, a phosphate ion, a sulfate ion, a carboxylate ion, or a negative ion of an organic acid.

11. The conductivity detector as claimed in claim 1, wherein the electrical conductivity of the ion component is obtained according to the following equation, $$C = \frac{\pi L}{4} \frac{D^2}{d}$$

where C denotes the electrical conductivity of the ion component, L denotes a specific conductivity of the ion component, D denotes the channel diameter, and d denotes the electrode gap by which the anode and the cathode are spaced apart.

12. An ion chromatography system, comprising:
a sample supplier to supply a sample solution into a flow of an eluent that is a moving phase of an ion chromatography, to thereby generate a multi-component solution in which a plurality of ion components is dissolved;
a separation column to sequentially separate the ion components from the multi-component solution to generate a plurality of single component solutions each having a single ion component and to sequentially discharge the single component solutions in a time order; and
a conductivity detector to detect a concentration of the single ion component in each of the single component solutions based on an electrical conductivity of the single ion component, wherein the conductivity detector includes:
a flow channel having a tube shape with a channel diameter through which the single component solution flows,
an electrode arrangement on the flow channel, the electrode arrangement including an anode and a cathode spaced apart by an electrode gap less than or equal to the channel diameter, and
a detector connected to the electrode arrangement to detect a voltage between the anode and the cathode corresponding to the electrical conductivity of the single ion component.

13. The ion chromatography system as claimed in claim 12, further comprising:
an eluent supplier having an eluent reservoir to store the eluent, and
a delivery pump to deliver the eluent from the eluent reservoir through the separation column and the conductivity detector.

14. The ion chromatography system as claimed in claim 12, wherein the sample supplier includes:
a sample dispenser to provide a fixed analysis quantity of the sample solution to a sample loop at a constant speed, and
an auto injector to automatically inject the sample solution of the sample loop to a flow path of the eluent.

15. The ion chromatography system as claimed in claim 12, wherein the separation column includes:
an ion exchange resin that is a stationary phase of the ion chromatography, the ion components in the multi-component solution sequentially separated according to a bonding strength between each of the ion components and a resin of the ion exchange resin.

16. The ion chromatography system as claimed in claim 12, wherein the flow channel includes:
an inlet enclosed by the anode and connected to the separation column into which the single component solution flows in,
an outlet enclosed by the cathode and out through which the single component solution flows, and
a flow cell between the inlet and the outlet and across which the single component solution passes to provide an ion flow from the inlet to the outlet.

17. The ion chromatography system as claimed in claim 12, further comprising:
a suppressor between the separation column and the conductivity detector to remove noise ions having a polarity opposite to the single ion component of the single component solution, the suppressor to remove noise from a signal of the electrical conductivity of the single ion component in the single component solution.

18. A detector, comprising:
a channel;
a first electrode on the channel; and
a second electrode on the channel,
wherein the channel is to carry a solution including ion components, wherein a gap between the first and second electrodes is less than or equal to a cross-sectional size of the channel, and wherein the first and second electrodes are to produce a voltage therebetween that is indicative of electrical conductivity of the ion components.

19. The detector as claimed in claim 18, wherein the cross-sectional size of the channel is substantially uniform from an inlet to an outlet of the channel.

20. The detector as claimed in claim 18, wherein the gap between the first and second electrodes is less than the cross-sectional size of the channel.

* * * * *